(12) United States Patent
Guevremont

(10) Patent No.: US 6,822,224 B2
(45) Date of Patent: Nov. 23, 2004

(54) TANDEM HIGH FIELD ASYMMETRIC WAVEFORM ION MOBILITY SPECTROMETRY (FAIMS)TANDEM MASS SPECTROMETRY

(75) Inventor: Roger Guevremont, Gloucester (CA)

(73) Assignee: National Research Council Canada, Ottawa (CA)

(*) Notice: Subject to any disclaimer, the term of this patent is extended or adjusted under 35 U.S.C. 154(b) by 1 day.

(21) Appl. No.: 10/220,605

(22) PCT Filed: Mar. 14, 2001

(86) PCT No.: PCT/CA01/00314
§ 371 (c)(1),
(2), (4) Date: Sep. 3, 2002

(87) PCT Pub. No.: WO01/69647
PCT Pub. Date: Sep. 20, 2001

(65) Prior Publication Data
US 2003/0020012 A1 Jan. 30, 2003

Related U.S. Application Data
(60) Provisional application No. 60/189,085, filed on Mar. 14, 2000.

(51) Int. Cl.[7] .......................... B01D 59/44; H01J 49/00; H01J 49/40; G01N 23/00
(52) U.S. Cl. ...................... 250/287; 250/281; 250/282; 250/286; 250/288; 250/289; 250/292; 250/297; 250/306; 250/307

(58) Field of Search ................. 250/281, 282, 250/286, 287, 288, 289, 292, 297, 306, 307

(56) References Cited

U.S. PATENT DOCUMENTS 3,668,383 A    6/1972  Carroll (List continued on next page.)

FOREIGN PATENT DOCUMENTS

| RU | 2105298 | 2/1998 |
| WO | WO 99/30350 A1 | 6/1999 |
| WO | WO 00/63949 A1 | 10/2000 |
| WO | WO 01/22049 A2 | 3/2001 |

OTHER PUBLICATIONS

U.S. patent application Ser. No. 09/762,238, Guevremont et al., not published.

(List continued on next page.)

*Primary Examiner*—Nikita Wells
*Assistant Examiner*—Mary El-Shammaa
(74) *Attorney, Agent, or Firm*—Freedman & Associates

(57) ABSTRACT

A tandem mass spectrometer is disclosed. A first mass analyzer within a low-pressure region is provided for passing ions therethrough. A collision cell is at an ion outlet of the mass analyzer to provide a location for ions to collide therein with a collision gas to form resultant ions. The resultant ions are then provided to a FAIMS analyzer for separation thereof and the separate resultant ions are provided to a mass analyzer for analysis.

30 Claims, 5 Drawing Sheets

U.S. PATENT DOCUMENTS

| | | | | |
|---|---|---|---|---|
| 4,234,791 A | * | 11/1980 | Enke et al. | 250/281 |
| 5,026,987 A | * | 6/1991 | Bier et al. | 250/281 |
| 5,073,713 A | * | 12/1991 | Smith et al. | 250/282 |
| 5,106,468 A | | 4/1992 | Chimenti | |
| 5,420,424 A | | 5/1995 | Carnahan et al. | |
| 5,523,566 A | * | 6/1996 | Fuerstenau et al. | 250/282 |
| 5,723,861 A | | 3/1998 | Carnahan et al. | |
| 5,736,739 A | | 4/1998 | Uber et al. | |
| 5,763,876 A | | 6/1998 | Pertinarides et al. | |
| 5,789,745 A | | 8/1998 | Martin et al. | |
| 5,801,379 A | | 9/1998 | Kouznetsov | |
| 5,847,386 A | | 12/1998 | Thomson et al. | |
| 5,869,831 A | | 2/1999 | De La Mora et al. | |
| 5,905,258 A | | 5/1999 | Clemmer et al. | |
| 6,015,972 A | * | 1/2000 | Hager | 250/282 |
| 6,040,573 A | * | 3/2000 | Sporleder et al. | 250/281 |
| 6,041,734 A | | 3/2000 | Raoux et al. | |
| 6,111,250 A | * | 8/2000 | Thomson et al. | 250/282 |
| 6,124,592 A | | 9/2000 | Spangler | |
| 6,162,709 A | | 12/2000 | Raoux et al. | |
| 6,184,522 B1 | * | 2/2001 | Jolliffe | 250/288 |
| 6,285,027 B1 | * | 9/2001 | Chernushevich et al. | 250/287 |
| 6,323,482 B1 | * | 11/2001 | Clemmer et al. | 250/287 |
| 6,495,823 B1 | | 12/2002 | Miller et al. | |
| 6,498,342 B1 | * | 12/2002 | Clemmer | 250/287 |
| 6,504,149 B2 | * | 1/2003 | Guevremont et al. | 250/286 |
| 6,512,224 B1 | | 1/2003 | Miller et al. | |
| 6,512,226 B1 | * | 1/2003 | Loboda et al. | 250/292 |
| 6,525,314 B1 | * | 2/2003 | Jarrell et al. | 250/297 |
| 6,534,764 B1 | * | 3/2003 | Verentchikov et al. | 250/287 |
| 6,621,077 B1 | | 9/2003 | Guevremont et al. | |
| 6,639,212 B1 | | 10/2003 | Guevremont et al. | |
| 6,653,627 B2 | | 11/2003 | Guevremont et al. | |
| 2001/0030285 A1 | | 10/2001 | Miller et al. | |
| 2002/0014586 A1 | | 2/2002 | Clemmer | |
| 2003/0020012 A1 | | 1/2003 | Guevremont et al. | |
| 2003/0038235 A1 | | 2/2003 | Guevremont et al. | |
| 2003/0057367 A1 | | 3/2003 | Guevremont et al. | |
| 2003/0057369 A1 | | 3/2003 | Guevremont et al. | |
| 2003/0089847 A1 | | 5/2003 | Guevremont et al. | |
| 2003/0089849 A1 | * | 5/2003 | Guevremont et al. | 250/287 |
| 2003/0150985 A1 | | 8/2003 | Guevremont et al. | |
| 2003/0213904 A9 | | 11/2003 | Guevremont et al. | |
| 2004/0004185 A9 | * | 1/2004 | Guevremont et al. | 250/287 |

OTHER PUBLICATIONS

U.S. patent application Ser. No. 09/762,238, Guevremont et al., not published.

Carr et al., "Plasma Chromatography", (1984), Plenum Press, New York.

Mason et al., "Transport Properties of Ions in Gases", (1988), Wiley, New York.

Buryakov et al., "A New Method of Separation of Multi-Atomic Ions by Mobility at Atmospheric Pressure using a High–Frequency Amplitude–Asymmetric Strong Electric Field", Int. J. Mass Spectrom. Ion Processes, No. 128, pp. 143–148, (1993), Elsevier Science Publishers B.V.

Eiceman et al., "Ion Mobility Spectrometry", (1994), CRC Press, Florida.

Carnahan et al., "Field Ion Spectrometry—A New Analytical Technology for Trace Gas Analysis", Proceedings of the 41st Annual ISA Analysis Division Symposium, paper #96–009, pp. 87–95, (1996), Framingham, MA, USA.

Guevremont et al., "Combined Ion Mobility/Time–of–Flight Mass Spectrometry Study of Electrospray–Generated Ions", Anal. Chem. 1997, vol. 69, No. 19, pp. 3959–3965, (Oct. 1, 1997), American Chemical Society.

Hudgins et al., "High Resolution Ion Mobility Measurements for Gas Phase Proteins: Correlation beteen Solution Phase and Gas Phase Conformations" Int. J. of Mass Spec. and Ion Processes 165/166, pp. 497–507, (1997), Elsevier Science Publishers B.V.

Riegner et al., "Qualitative Evaluation of Field Ion Spectrometry for Chemical Warfare Agent Detection", Proceedings of the 45th ASMS Conference on Mass Spectrometry and Allied Topics, Palm Springs, California, pp. 473, (1997).

Purves et al., "Mass Spectrometric Characterization of a High–Field Asymmetric Waveform Ion Mobility Spectrometer", Review of Scientific Instruments, vol. 69, No. 12, pp. 4094–4105, (Dec. 1998), American Institute of Physics.

Henderson et al., "ESI/Ion Trap/Ion Mobility/Time–of–Flight Mass Spectrometry for Rapid and Sensitive Analysis of Biomolecular Mixtures", Anal. Chem. 1999, vol. 71, No. 2, pp. 291–301, (Jan. 15, 1999), American Chemical Society.

Guevremont et al., "Atmospheric Pressure Ion Focusing in a High–Field Asymmetric Waveform Ion Mobility Spectrometer", Review of Scientific Instruments, vol. 70, No. 2, pp. 1370–1\383, (Feb. 1999), American Institute of Physics.

Krylov, "A Method of Reducing Diffusion Losses in a Drift Spectrometer", Tech. Phys., vol. 44, No. 1, pp. 113–116, (1999), American Institute of Physics.

* cited by examiner

TANDEM HIGH FIELD ASYMMETRIC WAVEFORM ION MOBILITY SPECTROMETRY (FAIMS)TANDEM MASS SPECTROMETRY

This application claims the benefit of U.S. Provisional Application No. 60/189,085 filed Mar. 14, 2000.

FIELD OF THE INVENTION

The present invention relates to an apparatus and method for separating ions, more particularly the present invention relates to an apparatus and method for separating ions based on the ion focusing principles of high field asymmetric waveform ion mobility spectrometry (FAIMS).

BACKGROUND OF THE INVENTION

High sensitivity and amenability to miniaturization for field-portable applications have helped to make ion mobility spectrometry (IMS) an important technique for the detection of many compounds, including narcotics, explosives, and chemical warfare agents as described, for example, by G. Eiceman and Z. Karpas in their book entitled "Ion Mobility Spectrometry" (CRC, Boca Raton, 1994). In IMS, gas-phase ion mobilities are determined using a drift tube with a constant electric field. Ions are gated into the drift tube and are subsequently separated in dependence upon differences in their drift velocity. The ion drift velocity is proportional to the electric field strength at low electric field strength, for example 200 V/cm, and the mobility, K, which is determined from experimentation, is independent of the applied electric field. Additionally, in IMS the ions travel through a bath gas that is at sufficiently high pressure such that the ions rapidly reach constant velocity when driven by the force of an electric field that is constant both in time and location. This is to be clearly distinguished from those techniques, most of which are related to mass spectrometry, in which the gas pressure is sufficiently low that, if under the influence of a constant electric field, the ions continue to accelerate.

E. A. Mason and E. W. McDaniel in their book entitled "Transport Properties of Ions in Gases" (Wiley, New York, 1988) teach that at high electric field strength, for instance fields stronger than approximately 5,000 V/cm, the ion drift velocity is no longer directly proportional to the applied field, and K becomes dependent upon the applied electric field. At high electric field strength, K is better represented by $K_h$, a non-constant high field mobility term. The dependence of $K_h$ on the applied electric field has been the basis for the development of high field asymmetric waveform ion mobility spectrometry (FAIMS), a term used by the inventors throughout this disclosure, and also referred to as transverse field compensation ion mobility spectrometry, or field ion spectrometry. Ions are separated in FAIMS on the basis of a difference in the mobility of an ion at high field strength, $K_h$, relative to the mobility of the ion at low field strength, K. In other words, the ions are separated because of the compound dependent behavior of $K_h$ as a function of the applied electric field strength. FAIMS offers a new tool for atmospheric pressure gas-phase ion studies since it is the change in ion mobility, and not the absolute ion mobility, that is being monitored.

The principles of operation of FAIMS using flat plate electrodes have been described by I. A. Buryakov, E. V. Krylov, E. G. Nazarov and U. Kh. Rasulev in a paper published in the International Journal of Mass Spectrometry and Ion Processes; volume 128 (1993), pp. 143–148, the contents of which are herein incorporated by reference. The mobility of a given ion under the influence of an electric field is expressed by: $K_h=K(1+f(E))$, where $K_h$ is the mobility of an ion at high electrical field strength, K is the coefficient of ion mobility at low electric field strength and f(E) describes the functional dependence of the ion mobility on the electric field strength. Ions are classified into one of three broad categories on the basis of a change in ion mobility as a function of the strength of an applied electric field, specifically: the mobility of type A ions increases with increasing electric field strength; the mobility of type C ions decreases; and, the mobility of type B ions increases initially before decreasing at yet higher field strength. The separation of ions in FAIMS is based upon these changes in mobility at high electric field strength. Consider an ion, for example a type A ion, which is being carried by a gas stream between two spaced-apart parallel plate electrodes of a FAIMS device. The space between the plates defines an analyzer region in which the separation of ions occurs. The net motion of the ion between the plates is the sum of a horizontal x-axis component due to the flowing stream of gas and a transverse y-axis component due to the electric field between the parallel plate electrodes. The term "net motion" refers to the overall translation that the ion, for instance said type A ion, experiences, even when this translational motion has a more rapid oscillation superimposed upon it. Often, a first plate is maintained at ground potential while the second plate has an asymmetric waveform, V(t), applied to it. The asymmetric waveform V(t) is composed of a repeating pattern including a high voltage component, V1, lasting for a short period of time t2 and a lower voltage component, V2, of opposite polarity, lasting a longer period of time t1. The waveform is synthesized such that the integrated voltage-time product, and thus the field-time product, applied to the plate during each complete cycle of the waveform is zero, for instance V1 t2+V2 t1=0; for example +2000 V for 10 μs followed by −1000 V for 20 μs. The peak voltage during the shorter, high voltage portion of the waveform is called the "dispersion voltage" or DV in this disclosure.

During the high voltage portion of the waveform, the electric field causes the ion to move with a transverse y-axis velocity component v1=$K_h$Ehigh, where Ehigh is the applied field, and $K_h$ is the high field ion mobility under ambient electric field, pressure and temperature conditions. The distance traveled is d1=v1t2=$K_h$Ehight2, where t2 is the time period of the applied high voltage. During the longer duration, opposite polarity, low voltage portion of the asymmetric waveform, the y-axis velocity component of the ion is v2=KElow, where K is the low field ion mobility under ambient pressure and temperature conditions. The distance traveled is d2=v2t1=KElowt1. Since the asymmetric waveform ensures that (V1 t2)+(V2 t1)=0, the field-time products Ehight2 and Elowt1 are equal in magnitude. Thus, if $K_h$ and K are identical, d1 and d2 are equal, and the ion is returned to its original position along the y-axis during the negative cycle of the waveform, as would be expected if both portions of the waveform were low voltage. If at Ehigh the mobility $K_h$>K, the ion experiences a net displacement from its original position relative to the y-axis. For example, positive ions of type A travel farther during the positive portion of the waveform, for instance d1>d2, and the type A ion migrates away from the second plate. Similarly, positive ions of type C migrate towards the second plate.

If a positive ion of type A is migrating away from the second plate, a constant negative dc voltage can be applied to the second plate to reverse, or to "compensate" for, this transverse drift. This dc voltage, called the "compensation voltage" or CV in this disclosure, prevents the ion from migrating towards either the second or the first plate. If ions derived from two compounds respond differently to the applied high strength electric fields, the ratio of Kh to K is similarly different for each compound. Consequently, the magnitude of the CV necessary to prevent the drift of the ion toward either plate is also different for each compound. Thus, when a mixture including several species of ions is being analyzed by FAIMS, only one species of ion is selectively transmitted for a given combination of CV and DV. The remaining species of ions, for instance those ions that are other than selectively transmitted through FAIMS, drift towards one of the parallel plate electrodes of FAIMS and are neutralized. Of course, the speed at which the remaining species of ions move towards the electrodes of FAIMS depends upon the degree to which their high field mobility properties differ from those of the ions that are selectively transmitted under the prevailing conditions of CV and DV.

An instrument operating according to the FAIMS principle as described previously is an ion filter, capable of selective transmission of only those ions with the appropriate ratio of Kh to K. In one type of experiment using FAIMS devices, the applied CV is scanned with time, for instance the CV is slowly ramped or optionally the CV is stepped from one voltage to a next voltage, and a resulting intensity of transmitted ions is measured. In this way a CV spectrum showing the total ion current as a function of CV, is obtained. It is a significant limitation of early FAIMS devices, which used electrometer detectors, that the identity of peaks appearing in the CV spectrum are other than unambiguously confirmed solely on the basis of the CV of transmission of a species of ion. This limitation is due to the unpredictable, compound-specific dependence of Kh on the electric field strength. In other words, a peak in the CV spectrum is easily assigned to a compound erroneously, since there is no way to predict or even to estimate in advance, for example from the structure of an ion, where that ion should appear in a CV spectrum. In other words, additional information is necessary in order to improve the likelihood of assigning correctly each of the peaks in the CV spectrum. For example, subsequent mass spectrometric analysis of the selectively transmitted ions greatly improves the accuracy of peak assignments of the CV spectrum.

In U.S. Pat. No. 5,420,424 which issued on May 30 1995, B. L. Carnahan and A. S. Tarassove disclose an improved FAIMS electrode geometry in which the flat plates that are used to separate the ions are replaced with concentric cylinders, the contents of which are herein incorporated by reference. The concentric cylinder design has several advantages, including higher sensitivity compared to the flat plate configuration, as was discussed by R. W. Purves, R. Guevremont, S. Day, C. W. Pipich, and M. S. Matyjaszczyk in a paper published in Reviews of Scientific Instruments; volume 69 (1998), pp 4094–4105. The higher sensitivity of the cylindrical FAIMS is due to a two-dimensional atmospheric pressure ion focusing effect that occurs in the analyzer region between the concentric cylindrical electrodes. When no electrical voltages are applied to the cylinders, the radial distribution of ions should be approximately uniform across the FAIMS analyzer. During application of DV and CV, however, the radial distribution of ions is not uniform across the annular space of the FAIMS analyzer region. Advantageously, with the application of an appropriate DV and CV for an ion of interest, those ions become focused into a band between the electrodes and the rate of loss of ions, as a result of collisions with the FAIMS electrodes, is reduced. The efficiency of transmission of the ions of interest through the analyzer region of FAIMS is thereby improved as a result of this two-dimensional ion focusing effect.

The focusing of ions by the use of asymmetric waveforms has been discussed above. For completeness, the behavior of those ions that are not focused within the analyzer region of a cylindrical geometry FAIMS is described here, briefly. As discussed previously, those ions having high field ion mobility properties that are other than suitable for focusing under a given set of DV, CV and geometric conditions will drift toward one or another wall of the FAIMS device. The rapidity with which these ions move towards the wall depends on the degree to which their $K_h/K$ ratio differs from that of the ion that is transmitted selectively under the prevailing conditions. At the very extreme, ions of completely the wrong property, for instance a type A ion versus a type C ion, are lost to the walls of the FAIMS device very rapidly.

The loss of ions in FAIMS devices should be considered one more way. If an ion of type A is focused, for example at DV 2500 volts, CV–11 volts in a given geometry, it would seem reasonable to expect that the ion is also focused if the polarity of DV and CV are reversed, for instance DV of –2500 volts and CV of +11 volts. This, however, is not observed and in fact the reversal of polarity in this manner creates a mirror image effect of the ion-focusing behavior of FAIMS. The result of such polarity reversal is that the ions are not focused, but rather are extremely rapidly rejected from the device. The mirror image of a focusing valley, is a hill-shaped potential surface. The ions slide to the center of the bottom of a focusing potential valley (2 or 3-dimensions), but slide off of the top of a hill-shaped surface, and hit the wall of an electrode. This is the reason for the existence, in the cylindrical geometry FAIMS, of the independent "modes" called 1 and 2. Such a FAIMS instrument is operated in one of four possible modes: P1, P2, N1, and N2. The "P" and "N" describe the ion polarity, positive (P) and negative (N). The waveform with positive DV, where DV describes the peak voltage of the high voltage portion of the asymmetric waveform, yields spectra of type P1 and N2, whereas the reversed polarity negative DV, waveform yields P2 and N1. The discussion thus far has considered positive ions but, in general, the same principles apply to negative ions equally.

A further improvement to the cylindrical FAIMS design is realized by providing a curved surface terminus of the inner electrode. The curved surface terminus is continuous with the cylindrical shape of the inner electrode and is aligned co-axially with an ion-outlet orifice of the FAIMS analyzer region. The application of an asymmetric waveform to the inner electrode results in the normal ion-focusing behavior described above, except that the ion-focusing action extends around the generally spherically shaped terminus of the inner electrode. This means that the selectively transmitted ions cannot escape from the region around the terminus of the inner electrode. This only occurs if the voltages applied to the inner electrode are the appropriate combination of CV and DV as described in the discussion above relating to 2-dimensional focusing. If the CV and DV are suitable for the focusing of an ion in the FAIMS analyzer region, and the physical geometry of the inner surface of the outer electrode does not disturb this balance, the ions will collect within a three-dimensional region of space near the terminus. Several contradictory forces are acting on the ions in this region near the terminus of the inner electrode. The force of the carrier gas flow tends to influence the ion cloud to travel towards the ion-outlet orifice, which advantageously also prevents the trapped ions from migrating in a reverse direction, back towards the ionization source. Additionally, the ions that get too close to the inner electrode are pushed back away from the inner electrode, and those near the outer electrode migrate back towards the inner electrode, due to the focusing action of the applied electric fields. When all forces acting upon the ions are balanced, the ions are effectively captured in every direction, either by forces of the flowing gas, or by the focusing effect of the electric fields of the FAIMS mechanism. This is an example of a three-dimensional atmospheric pressure ion trap, as disclosed in U.S. Pat. No. 6,621,077 issued on Sep. 16, 2003, in the name of Guevremont et al., the contents of which are herein incorporated by reference.

Ion focusing and ion trapping requires electric fields that are other than constant in space, normally occurring in a geometrical configuration of FAIMS in which the electrodes are curved, and/or are not parallel to each other. For example, a non-constant in space electric field is created using electrodes that are cylinders or a part thereof; electrodes that are spheres or a part thereof; electrodes that are elliptical spheres or a part thereof; and, electrodes that are conical or a part thereof. Optionally, various combinations of these electrode shapes are used.

As discussed above, one previous limitation of the cylindrical FAIMS technology is that the identity of the peaks appearing in the CV spectra are not unambiguously confirmed due to the unpredictable changes in Kh at high electric field strengths. Thus, one way to extend the capability of instruments based on the FAIMS concept is to provide a way to determine the make-up of the CV spectra more accurately, such as by introducing ions from the FAIMS device into a mass spectrometer for mass-to-charge (m/z) analysis. Advantageously, the ion focusing property of cylindrical FAIMS devices acts to enhance the efficiency for transporting ions from the analyzer region of a FAIMS device into an external sampling orifice, for instance an inlet of a mass spectrometer. This improved efficiency of transporting ions into the inlet of the mass spectrometer is optionally maximized by using a 3-dimensional trapping version of FAIMS operated in nearly trapping conditions. Under near-trapping conditions, the ions that have accumulated in the three-dimensional region of space near the spherical terminus of the inner electrode are caused to leak from this region, being pulled by a flow of gas towards the ion-outlet orifice. The ions that leak out from this region do so as a narrow, approximately collimated beam, which is pulled by the gas flow through the ion-outlet orifice and into a small orifice leading into the vacuum system of a mass spectrometer.

Additionally, the resolution of a FAIMS device is defined in terms of the extent to which ions having similar mobility properties as a function of electric field strength are separated under a set of predetermined operating conditions. Thus, a high-resolution FAIMS device transmits selectively a relatively small range of different ion species having similar mobility properties, whereas a low-resolution FAIMS device transmits selectively a relatively large range of different ion species having similar mobility properties. The resolution of FAIMS in a cylindrical geometry FAIMS is compromised relative to the resolution in a parallel plate geometry FAIMS because the cylindrical geometry FAIMS has the capability of focusing ions. This focusing action means that ions of a wider range of mobility characteristics are simultaneously focused in the analyzer region of the cylindrical geometry FAIMS. A cylindrical geometry FAIMS with narrow electrodes has the strongest focusing action, but the lowest resolution for separation of ions. As the radii of curvature are increased, the focusing action becomes weaker, and the ability of FAIMS to simultaneously focus ions of similar high-field mobility characteristics is similarly decreased. This means that the resolution of FAIMS increases as the radii of the electrodes are increased, with parallel plate geometry FAIMS having the maximum attainable resolution.

Note that, while the above discussion refers to the ions as being "captured" or "trapped", in fact, the ions are subject to continuous 'diffusion'. Diffusion always acts contrary to focusing and trapping. The ions always require an electrical, or gas flow force to reverse the process of diffusion. Thus, although the ions are focused into an imaginary cylindrical zone in space with almost zero thickness, or within a 3-dimensional ion trap, in reality it is well known that the ions are actually dispersed in the vicinity of this idealized zone in space because of diffusion. This is important, and should be recognized as a global feature superimposed upon all of the ion motions discussed in this disclosure. This means that, for example, a 3-dimensional ion trap actually has real spatial width, and ions continuously leak from the 3-dimensional ion trap, for several physical, and chemical reasons. Of course, the ions occupy a smaller physical region of space if the trapping potential well is deeper.

Of course, other apparatus for separating ions are known in the prior art, for instance an apparatus based on mass spectrometric techniques such as a radio-frequency quadrupole mass spectrometer. Further, tandem arrangements of such apparatus are known for producing collisionally induced dissociation of ionic species prior to a final mass analysis step, a field of study often referred to as tandem mass spectrometry. Of course, in many cases there are several possible fragment ions that have a same mass-to-charge ratio, and in the prior art tandem mass spectrometry system these ions are indistinguishable. It would be advantageous to provide a method and an apparatus to separate fragment ions which have a same mass-to-charge ratio in dependence upon a property of the ions other than a mass-to-charge ratio before providing the ions for the final mass analysis step.

OBJECT OF THE INVENTION

In order to overcome these and other limitations of the prior art, it is an object of the present invention to provide an apparatus for separating collisionally induced fragment ions having a substantially same mass-to-charge ratio prior to providing the fragment ions to a mass analyzer.

SUMMARY OF THE INVENTION

In accordance with the invention there is provided a tandem mass spectrometer comprising a first mass spectrometer within a low pressure region, a collision cell and a second mass analyzer within the low pressure region, characterized in that between the collision cell and the second mass spectrometer is disposed a FAIMS analyzer.

In accordance with another embodiment of the invention there is provided an apparatus for separating ions comprising:

a) a first analyzer region defined by a space between first and second spaced apart electrodes;

b) a collision region in operational communication with the first analyzer region for providing ions to the first analyzer region, the collision region defined by a space between two electrodes, the collision region having a first gas inlet, the first gas inlet for providing a flow of a collision gas within the collision region;

c) an ion source for providing ions to the collision region; and, f) a voltage source for providing at least a voltage to at least one of the first and second electrodes of the first analyzer region, to form an electric field therebetween, the electric field for effecting a separation of the resultant ions having an approximately same mass-to-charge ratio, wherein the ions provided to the first analyzer region include the collisionally induced fragment ions.

In accordance with another aspect of the invention there is provided a method for separating ions comprising the steps of:

providing ions to a mass spectrometer for transmission therethrough to a collision region having a collision gas therein;

colliding the ions with the collision gas to produce a plurality of resultant ions;

transporting the resultant ions through an electric field resulting from application of an asymmetric waveform to an electrode to perform a separation thereof; and, providing some of the separated ions to a mass spectrometer for analysis.

In accordance with yet another embodiment of the invention there is provided a method according to claim 20 wherein electric field is formed by the following steps:

i) providing a first asymmetric waveform and a first direct-current compensation voltage, to at least one electrode, to form an electric field therebetween, the first asymmetric waveform for effecting a difference in net displacement between two different ions in the time of one cycle of the applied first asymmetric waveform; and, ii) setting the first compensation voltage for effecting a separation of the fragment ions having an approximately same mass-to-charge ratio, to support selective transmission of the ions within the first analyzer region.

DETAILED DESCRIPTION OF THE INVENTION

Figure 1:
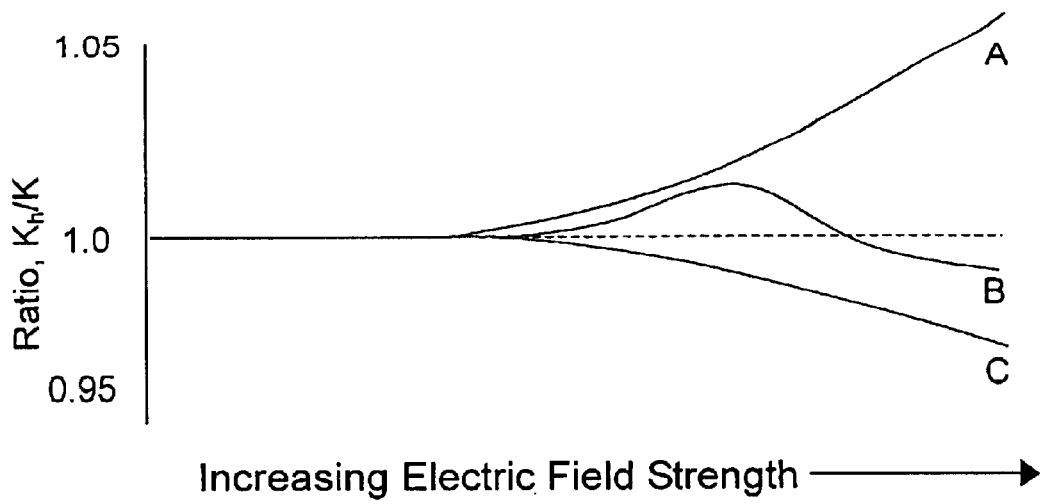
FIG. 1 shows three possible examples of changes in ion mobility as a function of the strength of an electric field.

Referring to FIG. 1, shown are three possible examples of the change in ion mobility properties with increasing electric field strength, as was discussed previously. The separation of ions in FAIMS is based upon a difference in these mobility properties for a first ion relative to a second ion. For instance, a first type A ion having a low field mobility K1,low is other than separated in a FAIMS device from a second type A ion having a second different low field mobility K2,low, if under the influence of high electric field strength, the ratio K1,high/K1,low is equal to the ratio K2,high/K2,low. Interestingly, however, this same separation is achieved using conventional ion mobility spectrometry, which is based on a difference in ion mobilities at low applied electric field strength.

Figure 2A:
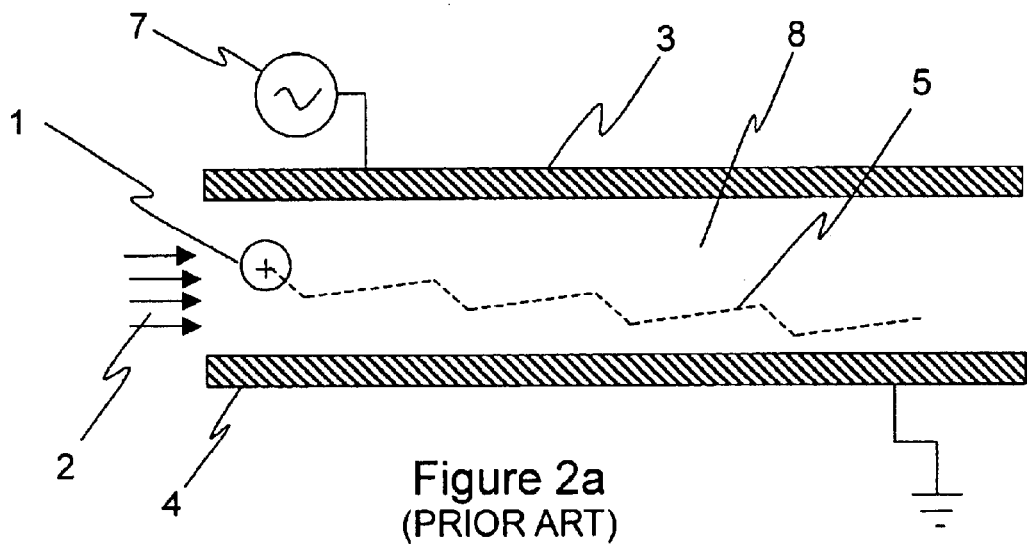
FIG. 2a illustrates the trajectory of an ion between two parallel plate electrodes under the influence of the electrical potential V(t)
Figure 2B:
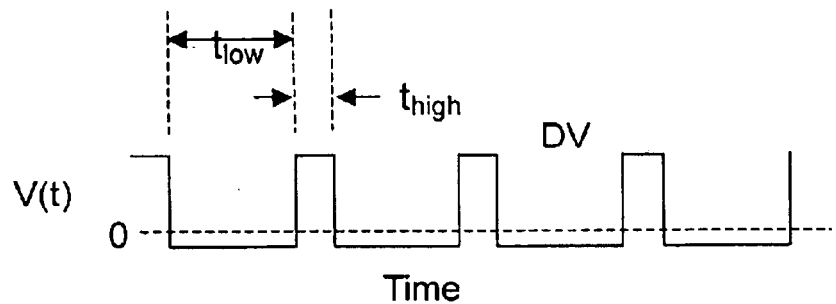
FIG. 2b shows an asymmetric waveform described by V(t)

Referring to FIG. 2a, shown is a schematic diagram illustrating the mechanism of ion separation according to the FAIMS principle. An ion 1, for instance a positively charged type A ion, is carried by a gas stream 2 flowing between two spaced apart parallel plate electrodes 3 and 4. One of the plates 4 is maintained at ground potential, while the other plate 3 has an asymmetric waveform described by V(t), applied to it by a voltage applier 7. The peak voltage applied during the waveform is called the dispersion voltage (DV), as is shown in FIG. 2b. Referring still to FIG. 2b, the waveform is synthesized so that the electric fields during the two periods of time $t_{high}$ and $t_{low}$ are not equal. If $K_h$ and K are identical at high and low fields, the ion 1 is returned to its original position at the end of one cycle of the waveform. However, under conditions of sufficiently high electric fields, $K_h$ is greater than K and the distances traveled during $t_{high}$ and $t_{low}$ are no longer identical. Within an analyzer region defined by a space 8 between the first and second spaced apart electrode plates, 3 and 4, respectively, the ion 1 experiences a net displacement from its original position relative to the plates 3 and 4 as illustrated by the dashed line 5 in FIG. 2a.

If a type A ion is migrating away from the upper plate 3, a constant negative dc compensation voltage CV is applied to plate 3 to reverse or "compensate" for this offset drift. Thus, the ion 1 does not travel toward either plate. If two species of ions respond differently to the applied high electric field, for instance the ratios of Kh to K are not identical, the compensation voltages necessary to prevent their drift toward either plate are similarly different. To analyze a mixture of ions, the compensation voltage is, for example, scanned to transmit each of the components of a mixture in turn. This produces a compensation voltage spectrum, or CV spectrum.

Figure 3:
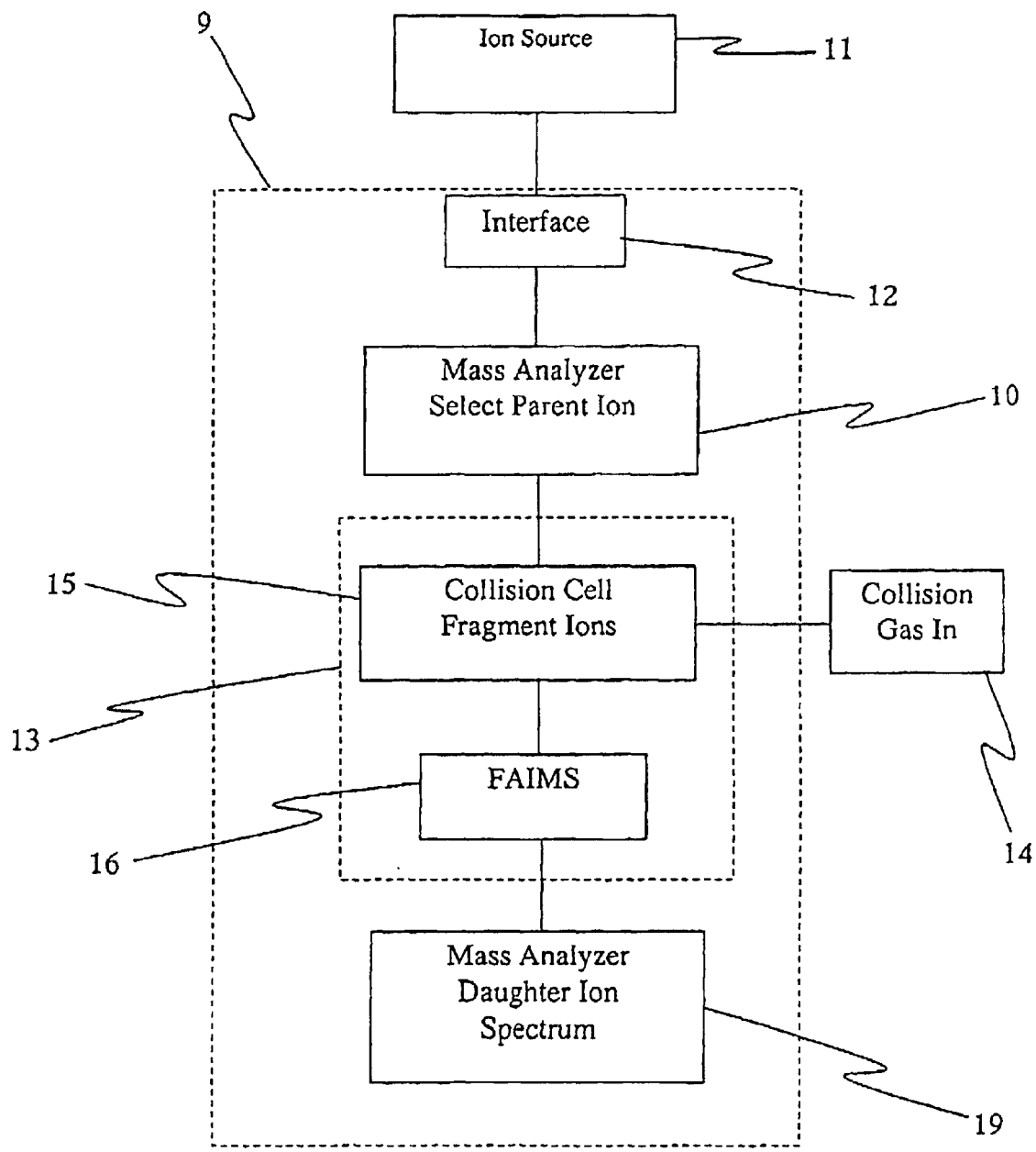
FIG. 3 shows a simplified block diagram of an MS/MS/FAIMS/MS system according to the present invention.

Referring to FIG. 3, a simplified block diagram of an MS/MS/FAIMS/MS system is shown. The ion source 11 is selected from a group including: electrospray ionization; corona discharge ionization; ionization by radioactivity; and, ionization by ultraviolet light. The ions are transferred into a low pressure region, for instance a vacuum chamber 9, through an interface 12, which optionally includes a differentially pumped region that serves to minimize the volume of gas which travels from the outside of the vacuum chamber into the vacuum chamber. Of course, if the ionization takes place at reduced pressure, for example within the vacuum chamber 9, then optionally electron impact ionization or chemical ionization are used to produce the ions. The interface 12 includes an orifice (not shown), which permits some of the ions produced by the ion source 11 to enter the vacuum chamber 9. The ions that pass through the interface 12 enter a first mass analyzer 10, which is optionally one of a quadrupole analyzer, an ion trap mass analyzer, and a time-of-flight mass spectrometer. Of course, other types of mass analyzers are known and are used optionally.

The mass analyzer 10 serves to separate an ion species of interest from a complex mixture of ions provided to the mass analyzer 10 through the interface 12. The ion species that are selected within mass analyzer 10 are transmitted to a high pressure chamber 13 which is supplied by a collision gas inlet 14. The transmitted ions are collided with a collision gas as they move longitudinally through the space between a set of rf-only quadrupoles of collision cell 15 within high pressure chamber 13 to fragment the ions into a plurality of smaller sub-units thereof. In the case of MS/MS experiments, it is usual to refer to the transmitted ions as the parent ions, and to the collisionally induced fragment ions as the daughter ions. The daughter ions have structure that is related to the structure of the parent ion. In normal practice the daughter ions are analyzed within another mass analyzer, and the identities of the daughter ions are determined to provide structural insights into the structure of the parent ion. Since the daughter ions have lower mass and are less complex than the original parent ions, it is in certain cases possible to deduce the structure of the parent ions from the identities of the daughter ions. This is typically one of the methods used to identify the structures of peptide molecules, which are the result of a tryptic digestion of a protein. By analyzing the peptide molecules, the structure of the protein is deduced. By analyzing the structures of the daughter ions that are produced from a collisional dissociation of the parent peptide ion, the structure of the peptide may be deduced. These complex experiments can be used to determine the primary sequence structure of proteins.

Still referring to FIG. 3, the fragment ions which are produced inside of the collision cell 15 are separated in FAIMS 16. FAIMS 16 is not used as the final mass analyzer, but rather is used to optionally separate ions which have equal m/z, and which would be other than separated in the final mass analyzer 19. A detector, not shown, registers the transmission of an ion through the system.

Advantageously, FAIMS separates ions independently of their m/z ratio. This has the important consequence that in many cases isobaric ions, for example two different species of ions having a same m/z ratio, are separated by FAIMS although they are other than separated by mass analyzers, including high resolution mass analyzers, which are extremely expensive instruments requiring bulky vacuum equipment and an expert operator. In contrast, the FAIMS device is relatively inexpensive, compact and simple to operate. It is a further advantage of FAIMS that the capability of FAIMS to separate ions having similar high field mobility properties improves, as the m/z ratio of the ion is decreased. This is completely consistent with the requirements of the system described herein, where FAIMS is required to separate fragment ions, rather than the parent ions which may have higher m/z. FAIMS is therefore ideally suited to separation of the ions produced by collisions of the parent ion with a bath gas.

Figure 4:
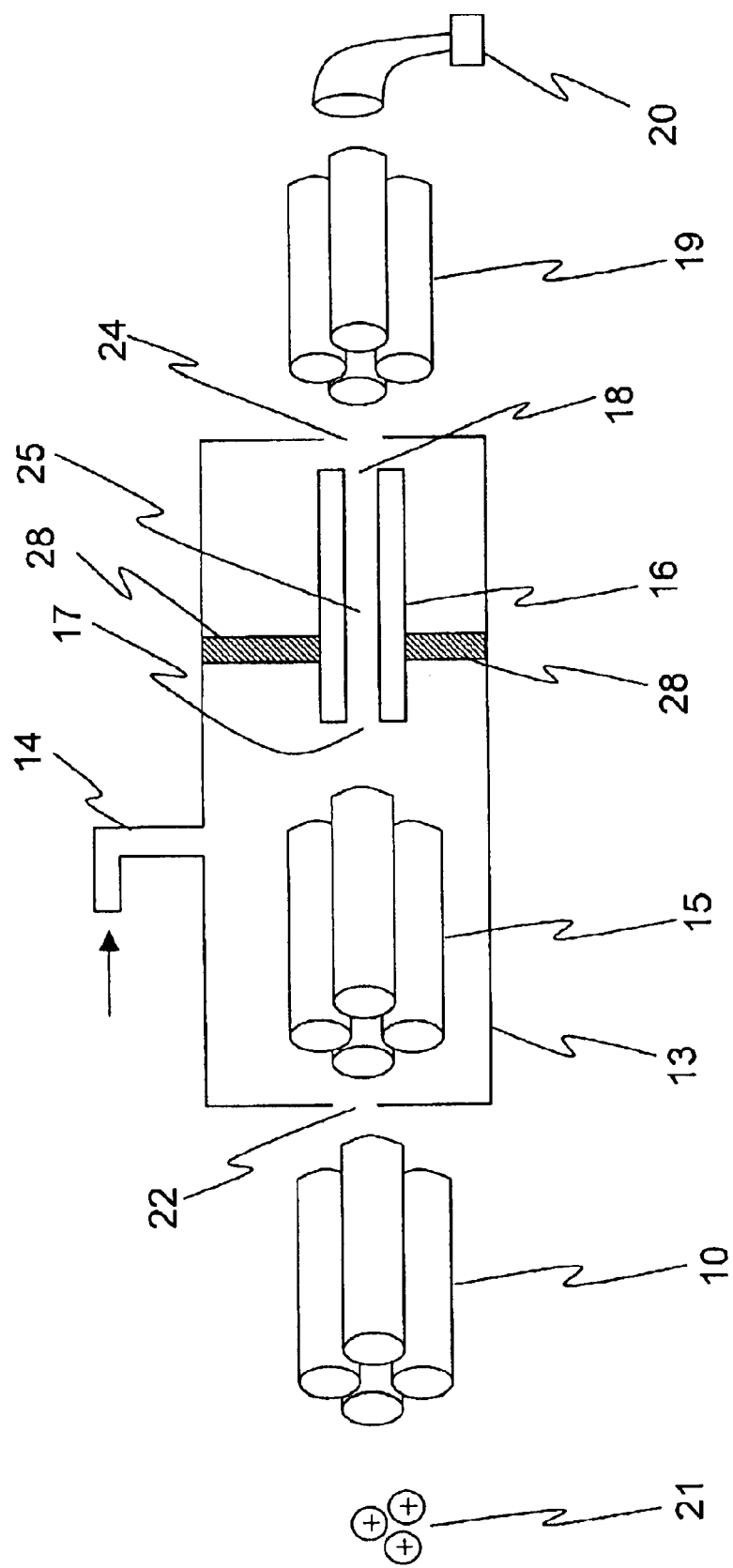
FIG. 4 shows a simplified block diagram of a MS/MS/FAIMS/MS system according to a first embodiment of the invention.

Referring to FIG. 4, a first preferred embodiment of the components mass analyzer 10, high pressure chamber 13, collision cell 15, FAIMS analyzer 16 and mass analyzer 19 are shown. The first mass analyzer is shown as a set of quadrupole rods 10, into which is flowing a mixture of ions 21. This analyzer 10 separates the mixture of ions 21, and transmits only ions of a substantially same m/z. The ions thus selected pass through an ion-inlet orifice 22 into a pressurized chamber 13 containing collision cell 15 and FAIMS 16. The collision gas enters the chamber 13 through a gas inlet 14 and because of the pumping system (not shown) which keeps the chamber 9 evacuated, the gas exits from high pressure chamber 13 through ion-inlet orifice 22 and an ion-outlet orifice 24.

Still referring to FIG. 4, the ions which enter the chamber 13 pass into collision cell 15, which includes a set of rf-only quadrupole rods for physically confining the parent ions and the resultant daughter ions within the center longitudinal axis of the quadrupole rod structure. A mixture including the original parent ions and the collisionally produced fragments are passed out of the collision cell 15 and pass into a FAIMS apparatus 16 comprising at least first and second spaced apart electrodes, defining an analyzer region 25 therebetween. By application of an asymmetric waveform, and a compensation voltage to at least one of the first and second electrodes of FAIMS, an ion with the appropriate change in high field mobility properties relative to its low field mobility properties is selected from the mixture of fragment ions provided from the collision cell 15. An electrical controller (not shown) is connected to at least one of the first and second electrodes for, in use, applying the asymmetric waveform, and a compensation voltage to effect ion separation. The ions are carried through the FAIMS analyzer region 25 by the flow of gas which is exiting through the ion-outlet orifice 24. The ions with the appropriate properties are transmitted through the analyzer region 25 of FAIMS device 16, and out of the ion-outlet orifice 24 of the high pressure chamber 13. Higher or lower flows of gas along the length of the analyzer can be achieved by optionally placing appropriate baffles 28 mounted around the FAIMS 16 to modify the difference in gas pressure before entrance of FAIMS in region 17 relative to the pressure at the outlet region of FAIMS in region 18. Optionally, high pressure chamber 13 is structurally divided into two compartments one of which houses the collision cell 15, and the second of which houses the FAIMS 16.

Still referring to FIG. 4, the ions which exit from ion-outlet orifice 24 in the high pressure chamber 13 are mass analyzed by quadrupole assembly 19. A detector 20 is used to register those ions which are transmitted through the system.

The FAIMS 16 shown in FIG. 4 comprises first and second spaced-apart parallel plate electrodes, defining an analyzer region 25 therebetween. Of course, other FAIMS electrode geometries are known and are optionally used in place of the two-electrode parallel plate FAIMS shown in FIG. 4. For instance, a FAIMS device is selected from the group including: FAIMS comprising n curved electrode bodies (n≧2); FAIMS comprising n parallel, flat plate electrodes (n≧2); and, FAIMS comprising at least first and second coaxially aligned and substantially overlapping concentric cylindrical electrodes. Further optionally, a curved surface is provided along at least one of the leading and trailing edges of at least an electrode of the FAIMS according to any of the above electrode geometries for further focusing the ions to achieve improved ion transmission efficiency through the FAIMS 16.

The system shown in FIG. 4 suffers one limitation which is overcome by using a novel arrangement of electrodes in FAIMS. If the FAIMS device 16 in FIG. 4 is not needed, for example the separation of isobaric daughter ions produced within the rf-only quadrupole assembly 15 is other than required, then the efficiency of ion transmission through the FAIMS 16 limits the overall sensitivity of the system. Although it is practical to remove a FAIMS which is coupled external to the vacuum chamber 9, the removal of FAIMS 16 within the vacuum chamber 9 as shown in FIG. 4 is other than practical.

Figure 5:
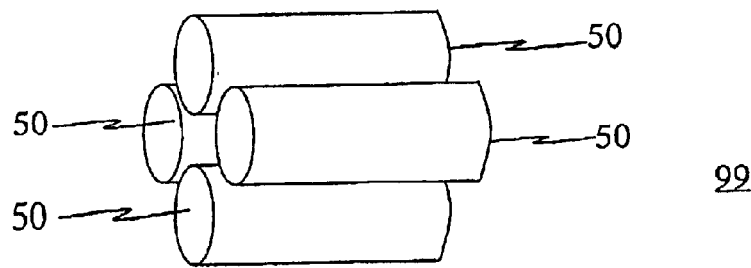
FIG. 5 shows a simplified schematic diagram of a FAIMS analyzer useable in the system according to the present invention.
Figure 8:
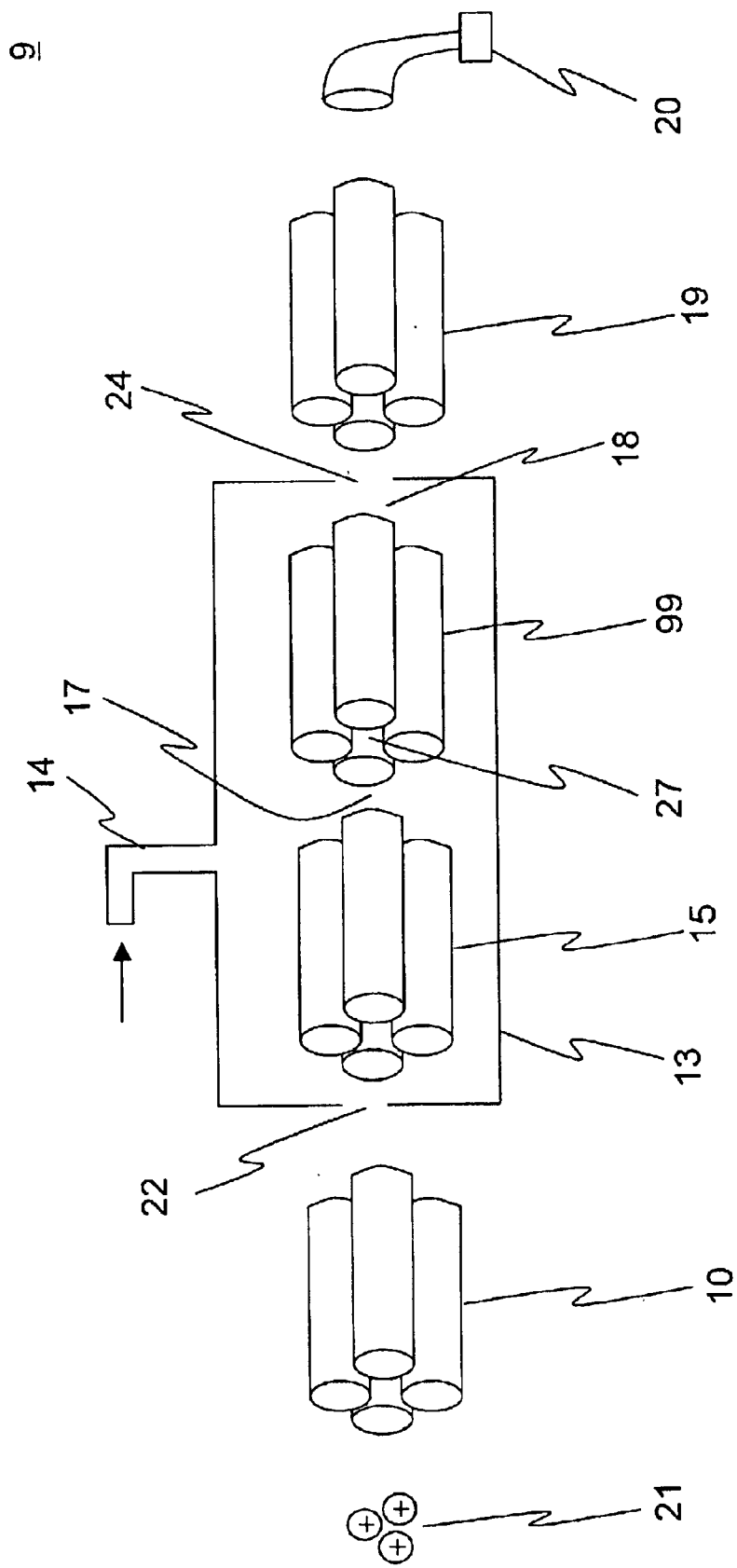

Referring to FIG. 5 and to FIG. 8, shown is a FAIMS 99 which is built in the same physical configuration as a quadrupole mass analyzer, comprising four parallel rods 50. The electrode geometry shown schematically in FIG. 5 FAIMS is usable as a FAIMS analyzer by application of an asymmetric waveform to at least a parallel rod electrode 50. The remaining rods may be maintained at some other fixed dc voltage. If the asymmetric waveform is applied to one of the four rods, the other three act as the fixed, constant voltage counter electrode. The electric fields between the rods 50 permits the separation of ions in exactly the manner described previously for FAIMS of other physical geometries.

Figure 6:
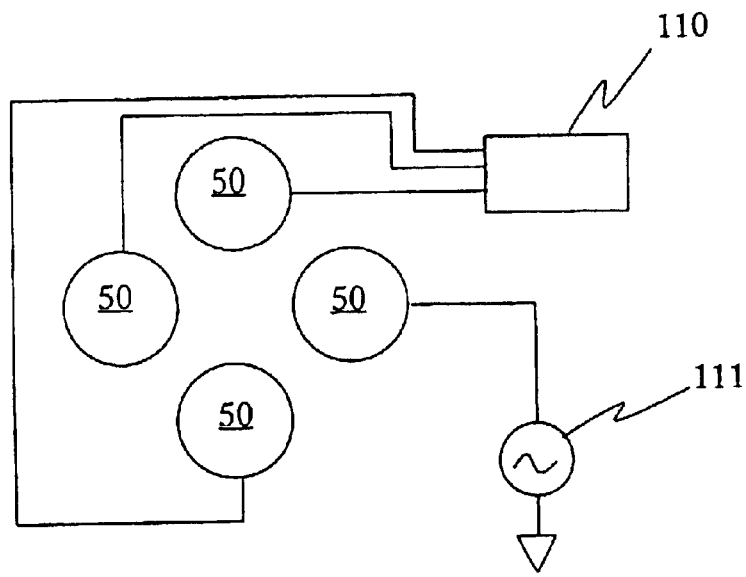
FIG. 6 shows a first possible electrical connection to the FAIMS analyzer of FIG. 5.

Referring now to FIG. 6, shown is a first possible electrical connection to the quadrupole FAIMS described with reference to FIG. 5. The asymmetric waveform is generated in a supply 111 and provided to one rod 50 of the set of four rods 50. In this case, the remaining three rods 50 are held at constant voltage by one of grounding to zero volts, and by application of dc voltages through supply 110.

Figure 7:
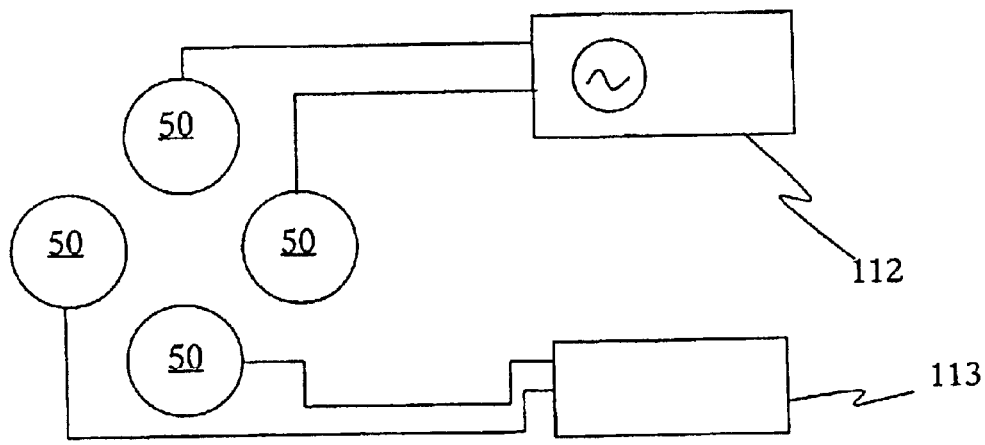
FIG. 7 shows a second possible electrical connection to the FAIMS analyzer of FIG. 5; and, FIG. 8 shows a simplified block diagram of a MS/MS/FAIMS/MS system, including the FAIMS analyzer of FIG. 5, according to a second embodiment of the invention.

Referring to FIG. 7, shown is a second possible electrical connection to quadrupole FAIMS described with reference to FIG. 5. The asymmetric waveform is generated in a supply 112 and provided to a pair of adjacent rods 50. The remaining pair of rods 50 are held at constant voltage by one of grounding to zero volts, and by application of dc voltages through supply 113.

In other systems there is no advantage to the quadrupole structure, however, in the system described with reference to FIG. 5 through FIG. 8, the quadrupole rods 50 are advantageous because the FAIMS is in effect removed from the system by application of the regular sinusoidal waveforms to the rods. This means that the electrical controls (not shown) to the rods from outside of the vacuum system permits the set of rod 99 to function as one of a FAIMS and a rf-only quadrupole, but not at a same time. Optionally, the set of rod 99 functions as a quadrupuole mass analyzer.

Referring again to FIG. 8, the first mass analyzer is shown as a series of quadrupole rods into which is flowing a mixture of ions 21. This analyzer 10 separates the mixture of ions 21, and transmits only ions of a substantially same m/z. The ions thus selected pass through an ion-inlet orifice 22 into a high pressure chamber 13. The collision gas enters the chamber 13 through a gas inlet 14 and because of the pumping system (not shown) which keeps the chamber evacuated, the gas exits from chamber 13 through ion-inlet orifice 22 and an ion-outlet orifice 24. The ions which enter the chamber 13 pass into collision cell 15, which includes a set of rf-only quadrupole rods for physically confining the parent ions and the resultant daughter ions within the center longitudinal axis of the quadrupole rod structure. A mixture including the original parent ions and the collisionally produced fragments are passed out of collision cell 15 and pass into a FAIMS apparatus 99 comprising four parallel rods defining an analyzer region 27 therebetween. By application of an asymmetric waveform, and a compensation voltage to at least one of the four parallel rod electrodes of FAIMS, an ion with the appropriate change in high field mobility properties relative to its low field mobility properties is selected from the mixture of fragment ions provided from the collision cell 15. An electrical controller (not shown) is connected to at least one of the four parallel rod electrodes for, in use, applying the asymmetric waveform, and a compensation voltage to effect ion separation. The ions are carried through the FAIMS analyzer region 27 by the flow of gas which is exiting through the ion-outlet orifice 24. The ions with the appropriate properties are transmitted through the analyzer region 27 of FAIMS device 99, and out of the ion-outlet orifice 24 of the high pressure chamber 13. Higher or lower flows of gas along the length of the analyzer can be achieved by optionally mounting appropriate baffles (not shown) around the FAIMS 99 to modify the difference in gas pressure before entrance of FAIMS in region 17 relative to the pressure at the outlet region of FAIMS in region 18. Optionally, high pressure chamber 13 is structurally divided into two compartments one of which houses the collision cell 15, and the second of which houses the FAIMS 99.

Still referring to FIG. 8, the ions which exit from ion-outlet orifice 24 in the high pressure chamber 13 are mass analyzed by quadrupole assembly 19. A detector 20 is used to register those ions which are transmitted through the system.

Optionally, the two separate sets of quadrupole rods of collision cell 15 and FAIMS 99 are merged into a single set of segmented rods having small electrically insulating regions between closely space, longitudinally aligned rods. Further optionally, the two separate sets of quadrupole rods of collision cell 15 and FAIMS 99 are replaced by a single set of rods. The ions entering this cell would be fragmented during collisions with a gas held in the cell 13, but instead of a rf-only quadruupole operation, the electrical signals to the rods would be set for operation as FAIMS. This is accomplished by application of an asymmetric waveform to at least one, but not all, of the rods. By application of the appropriate DV and CV for the prevailing bath gas number density conditions in the cell, separation of ions based on the difference of ion mobility properties at high and low electric fields is accomplished, and in normal operation of FAIMS. If FAIMS is not needed, the quadrupole assembly is operated in the normal fashion by application of sinusoidal waveforms to the pairs of opposite rods, as is well known in the field of mass spectrometry. The need to physically remove the FAIMS apparatus from the system when other than in use is therefore eliminated.

Of course, numerous other embodiments could be envisioned, without departing significantly from the teachings of the present invention.

What is claimed is:

1. A tandem mass spectrometer comprising a first mass analyzer within a low pressure region, a collision cell and a second mass analyzer within the low pressure region, characterized in that between the collision cell and the second mass analyzer is disposed a FAIMS analyzer.

2. An apparatus according to claim 1, wherein the collision cell is disposed within a chamber for containing a collision gas.

3. An apparatus according to claim 1, wherein the FAIMS analyzer comprises:

first and second spaced apart electrodes defining a FAIMS analyzer region therebetween, the FAIMS analyzer region having a first ion inlet and a first ion outlet, the first ion inlet for, in use, receiving ions for introduction into the FAIMS analyzer region, the first ion outlet for, in use, providing ions from the FAIMS analyzer region.

4. An apparatus according to claim 3, wherein the FAIMS analyzer comprises:

at least a first voltage source for providing an asymmetric waveform and a direct-current compensation voltage to at least one of the first and second spaced apart electrodes, to form a first electric field therebetween, the asymmetric waveform for, in use, effecting a difference in net displacement between the ions in the time of one cycle of the applied asymmetric waveform and the compensation voltage for, in use, effecting a first separation of the ions supporting selective transmission of the ions within the FAIMS analyzer region.

5. An apparatus according to claim 4, wherein the low pressure region is a low pressure region within a vacuum chamber.

6. An apparatus according to claim 5, comprising a second chamber within the vacuum chamber, the second chamber having a second ion inlet, a second ion outlet and a gas inlet, the second ion inlet for, in use, introducing ions into second chamber and out of the second ion outlet, the gas inlet for introducing at least a gas having a predetermined composition into the second chamber to define at least a high pressure region.

7. An apparatus according to claim 6, wherein the collision cell and the FAIMS analyzer are disposed within the second chamber, the collision cell in fluid communication with the second ion inlet.

8. An apparatus according to claim 7, comprising a partition for segmenting the second chamber into at least two compartments, the at least two compartments in fluid communication one with the other and wherein the collision cell and the FAIMS analyzer are each disposed within a different compartment of the second chamber.

9. An apparatus according to claim 6, wherein the collision cell is disposed within the second chamber and comprising a third chamber including an ion inlet, an ion outlet and housing the FAIMS, the third chamber in fluid communication with the second chamber.

10. An apparatus according to claim 3, wherein the FAIMS analyzer comprises:
a first voltage source for providing a voltage having an approximately sinusoidally varying amplitude to at least one of the first and second spaced apart electrodes of the FAIMS, to form a first electric field therebetween, the first electric field for transmitting ions through the FAIMS analyzer such that ions are other than separated by FAIMS.

11. An apparatus according to claim 10, wherein the collision cell and the FAIMS analyzer are disposed within separate chambers for containing a pressure, such that the FAIMS analyzer is operable in a first mode under low pressure and in a second other mode under higher pressure independent of the pressure within the chamber housing the collision cell.

12. An apparatus according to claim 11, wherein the FAIMS analyzer comprises third and fourth electrodes, arranged such that the four electrodes of the FAIMS analyzer are disposed along corner edges of a quadrilateral solid.

13. A tandem mass spectrometer comprising a first mass analyzer within a low pressure region; a FAIMS for providing a collision cell and ion separation; and a second mass analyzer within a low pressure region.

14. An apparatus according to claim 13, wherein the FAIMS analyzer comprises:
first and second spaced apart electrodes defining a FAIMS analyzer region therebetween, the FAIMS analyzer region having a first ion inlet and a first ion outlet, the first ion inlet for, in use, receiving ions for introduction into the FAIMS analyzer region, the first ion outlet for, in use, providing ions from the FAIMS analyzer region.

15. An apparatus according to claim 14, wherein the FAIMS analyzer comprises:
at least a first voltage source for providing an asymmetric waveform and a direct-current compensation voltage to at least one of the first and second spaced apart electrodes, to form a first electric field therebetween, the asymmetric waveform for, in use, effecting a difference in net displacement between the ions in the time of one cycle of the applied asymmetric waveform and the compensation voltage for, in use, effecting a first separation of the ions supporting selective transmission of the ions within the FAIMS analyzer region.

16. An apparatus according to claim 15, wherein the FAIMS analyzer is disposed within a chamber for containing a pressure, such that the FAIMS analyzer is operable in a first mode under low pressure and in a second other mode under higher pressure.

17. An apparatus according to claim 16, wherein the FAIMS analyzer comprises third and fourth electrodes, arranged such that the four electrodes of the FAIMS analyzer are disposed along corner edges of a quadrilateral solid.

18. The apparatus according to claim 13, wherein the FAIMS analyzer comprises:
four electrodes disposed approximately along corner edges of a quadralateral solid for transmitting ions through a low pressure region in a first mode of operation and for providing a field for effecting a separation of ions in a second other mode of operation.

19. An apparatus for separating ions comprising:
a) a FAIMS analyzer region defined by a space between first and second spaced apart electrodes;
b) a collision region in operational communication with the FAIMS analyzer region for providing ions to the FAIMS analyzer region, the collision region defined by a space between two electrodes, the collision region having a first gas inlet, the first gas inlet for providing a flow of a collision gas within the collision region;
c) an ion source for providing ions to the collision region; and,
d) a voltage source for providing at least a voltage to at least one of the first and second electrodes of the FAIMS analyzer region, to form an electric field therebetween, the electric field for effecting a separation of the provided ions having an approximately same mass-to-charge ratio,
wherein the ions provided to the collision region interact with the collision gas to produce collisionally induced fragment ions, and wherein the ions provided to the FAIMS analyzer region include the collisionally induced fragment ions.

20. A method for separating ions comprising:
providing ions to a first mass analyzer for transmission therethrough to a collision region having a collision gas therein;
colliding the ions with the collision gas to produce a plurality of resultant ions;
transporting the resultant ions through an electric field resulting from application of an asymmetric waveform to an electrode to perform a separation thereof; and,
providing some of the separated ions to a second mass analyzer for analysis.

21. A method for separating ions according to claim 20, wherein the resultant ions are collisionally induced fragment ions.

22. A method according to claim 20, wherein electric field is formed by:
i) providing a first asymmetric waveform and a first direct-current compensation voltage, to at least one electrode, to form an electric field therebetween, the first asymmetric waveform for effecting a difference in net displacement between two different ions in the time of one cycle of the applied first asymmetric waveform; and,
ii) setting the first compensation voltage for effecting a separation of the fragment ions having an approximately same mass-to-charge ratio, to support selective transmission of the ions within the first analyzer region.

23. A method according to claim 20, including detecting the selectively transmitted ions by mass spectrometry.

24. A method according to claim 23, wherein the collisions and the electric field are disposed within at least a high-pressure region.

25. A method according to claim 24, wherein the at least a high-pressure region is disposed within a chamber within a low-pressure region.

26. A method according to claim 25, wherein the low pressure region is a low-pressure region of a vacuum chamber.

27. A method according to claim 22, wherein the electrodes are shaped for focusing the ions in a predetermined fashion.

28. A method according to claim 27, wherein the electrodes are selected from the group including: flat parallel plates; curved plates; cylinders; and, parallel rods.

29. A method according to claim 28, wherein the voltage applied to the electrode has an amplitude varying in a sinusoidal fashion over time for operating the first analyzer region in an RF-only mode in which ions are other than separated by FAIMS.

30. The method according to claim 28, wherein the electric field is provided between at least two pairs of electrodes and wherein the voltage applied to the electrode has an amplitude varying in a sinusoidal fashion over time and a dc voltage.

* * * * *